United States Patent [19]

Murphy

[11] 4,270,538
[45] Jun. 2, 1981

[54] BREAST SHIELD

[76] Inventor: Michael K. Murphy, 21 Hillcrest Dr., San Rafael, Calif. 94901

[21] Appl. No.: 72,954

[22] Filed: Sep. 6, 1979

Related U.S. Application Data

[63] Continuation of Ser. No. 847,281, Oct. 31, 1977, abandoned.

[51] Int. Cl.³ .......................... A61M 1/08; A41C 3/00
[52] U.S. Cl. ..................................... 128/282; 128/461
[58] Field of Search ............... 128/280, 282, 461, 150; 220/90.4, 1 C, DIG. 27

[56] References Cited

U.S. PATENT DOCUMENTS

| 2,414,697 | 1/1947 | Pettersson | 220/90.4 |
| 3,840,012 | 10/1974 | Rushton, Jr. | 128/280 |

FOREIGN PATENT DOCUMENTS

| 23719 | 12/1921 | France | 220/90.4 |
| 1143628 | 10/1957 | France | 128/282 |
| 63985 | 3/1949 | Netherlands | 128/282 |
| 6740 | of 1889 | United Kingdom | 128/282 |

Primary Examiner—Robert W. Michell
Assistant Examiner—C. W. Shedd
Attorney, Agent, or Firm—Townsend and Townsend

[57] ABSTRACT

A two-piece breast shield to be worn by a nursing woman is disclosed. A base, contoured to confront the wearer's breast, has an aperture through which the nipple can pass. A dome-shaped cover overlies the base, fitting onto it to define an interior milk-receiving chamber. A small vent hole near the edge of the cover is surrounded by an inwardly extending tube to prevent milk from flowing out through the hole when the woman wearing the breast shield bends over.

2 Claims, 8 Drawing Figures

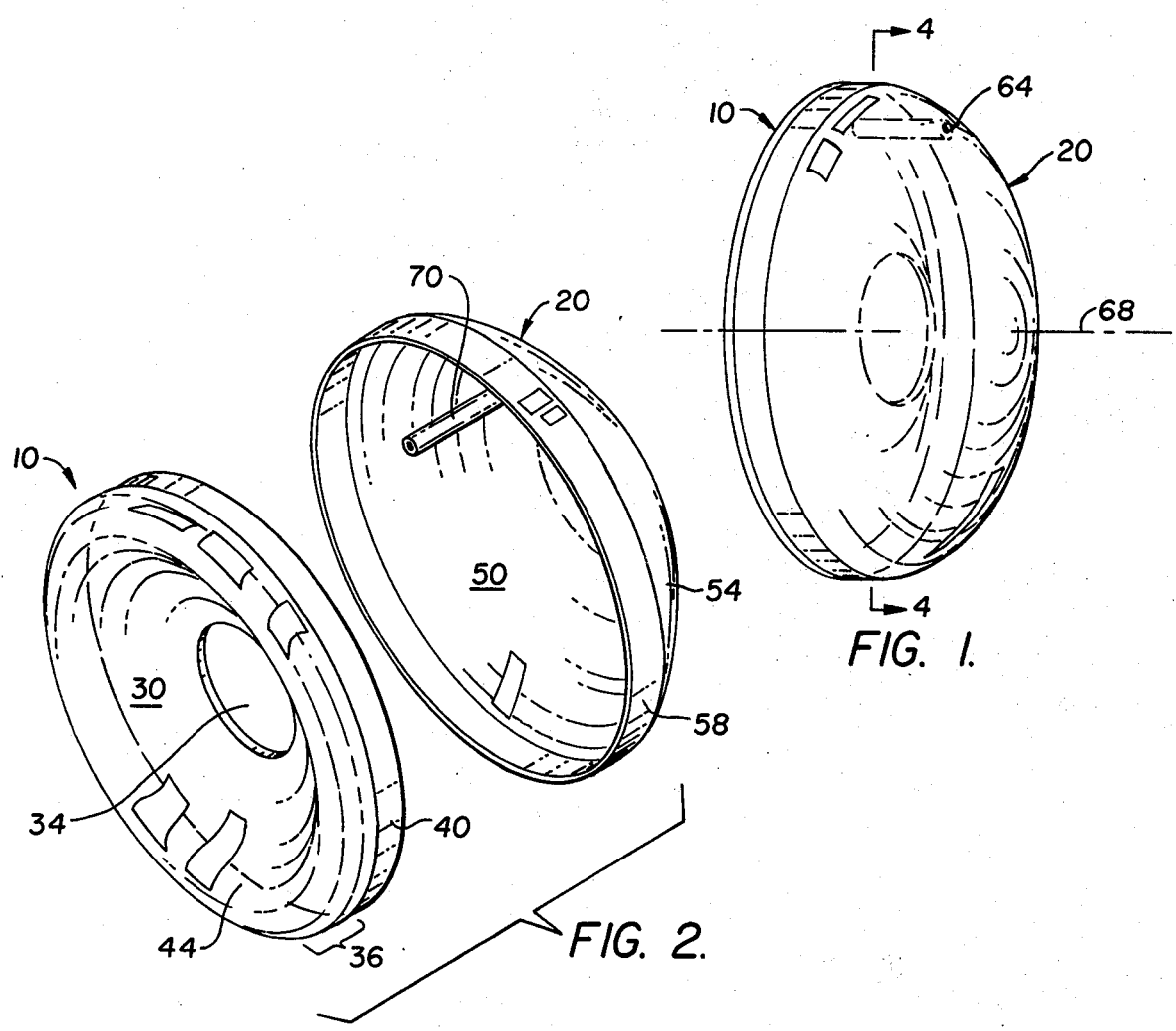
FIG. 1.
FIG. 2.
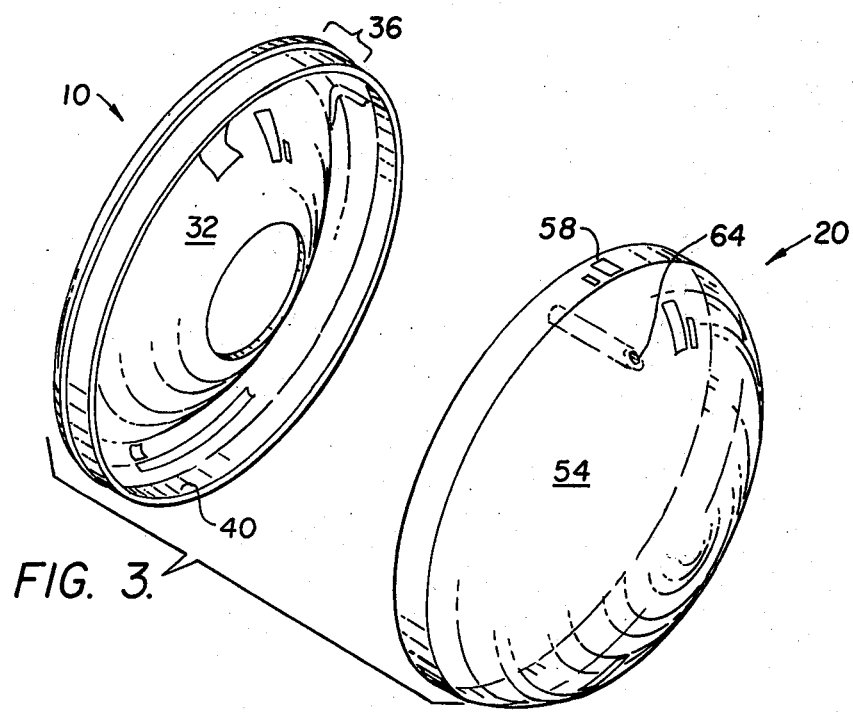
FIG. 3.

BREAST SHIELD

This is a continuation of application Ser. No. 847,281, filed Oct. 31, 1977, now abandoned.

BACKGROUND OF THE INVENTION

This invention relates to breast shields that also function as milk collectors.

While breast feeding of infants is thought by many to provide numerous advantages, including overall convenience, it is not without its own inconveniences. The two major problems tend to be soreness of the nipple and leakage of milk between feedings. It is with these problems in mind that numerous devices have been developed.

U.S. Pat. No. 3,840,012 to Rushton, Jr., discloses a two-piece hollow breast shield which also functions as a milk collector. The device has a breast-confronting base and an overlying exterior cover. Such a hollow device fitting over the breast presents at least two problems. First, the very shape of the breast shield makes it likely that a vacuum will form within the milk receiving chamber. This would make removal of the device painful, and might even cause damage to the already delicate tissues.

Second, it is awkward to recover for use the milk that has collected within the device. Generally it will be necessary to disassemble the device, taking care that the cover is kept in a level position so that the milk accumulated therein is not spilled until it is poured out. The extra handling during disassembly increases the possibility of contamination and enhances the chance of spilling the collected milk, as for example by dropping the cover.

A solution for these problems, suggested by Rushton, is the provision of a small orifice in the cover near the top of the device for pouring out the collected milk. This small orifice also vents the interior of the breast shield, thereby preventing the formation of a vacuum within it.

However, this proposed solution has its own difficulty. When a woman who is wearing the breast shield in which milk has collected bends over, the milk leaks out of the small hole. The woman's clothing is soiled, and if the leakage extends to the woman's outer garments, it may prove to be a source of embarrassment. Thus, the effort to solve the aforementioned venting and emptying problems has led to a device with the same "leaking" problem that it was a major object of the breast shield to eliminate.

Accordingly, it is an object of this invention to provide a breast shielding, milk collecting device which provides a vented interior and yet does not suffer from the "leakage" problem.

SUMMARY OF THE INVENTION

A two-piece breast shield, preferably fabricated from slightly flexible plastic, also functions as a milk collector. The device fits over a woman's breast and is typically held in place by a brassiere. A round base having a concave breast-confronting surface and a convex chamber defining surface is provided with a central aperture for the nipple to pass through. A peripheral lip surrounds the convex chamber defining surface and extends away from the breast when the device is worn. A dome-shaped cover having a concave chamber defining surface and an outer convex surface fits over the base without contacting the nipple. Thus, the nipple is protected from contact with the brassiere. A peripheral lip surrounds the concave chamber defining surface and has an inner diameter substantially equal to the outer diameter of the lip surrounding the convex chamber defining surface on the base. Thus, when the base and the cover are pressed together, the peripheral lips hold the unit as one piece to provide a milk receiving chamber within. A small orifice is provided near the edge of the cover, and is positioned near the top of the shield when the shield is in place.

Leakage and spillage through the small orifice is prevented by an inwardly extending tube surrounding the orifice and extending into the chamber from the concave chamber defining surface. Thus, when a woman wearing the breast shield in which milk has accumulated bends over, the tube acts as a dam around the orifice and prevents the loss of milk through the orifice. If the wearer of the shield wishes to empty the milk out without disassembling the shield, she can do this by rotating the shield 180 degrees from its normal position. The orifice, surrounded by the tube, is then at the bottom position of the shield. The tube is submersed in the milk which is then able to flow out of the orifice.

BRIEF DESCRIPTION OF THE DRAWINGS

FIG. 1 is a perspective view from the front showing the breast shield in its assembled state.

FIG. 2 is a perspective view from the rear, showing the breast shield disassembled.

FIG. 3 is a perspective view from the front showing the breast shield disassembled.

DESCRIPTION OF THE PREFERRED EMBODIMENT

Figure 4:
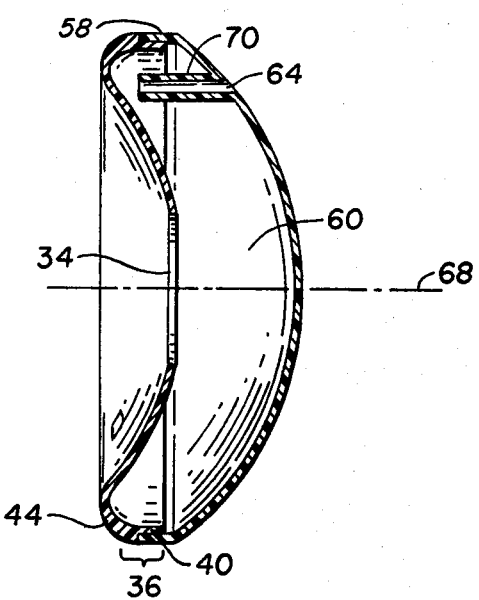
FIG. 4 is a sectional view along the line 4—4 of FIG. 1.

FIG. 1 shows base 10 and cover 20 assembled so that the breast shield is ready for wearing. The parts are typically constructed of slightly flexible plastic, preferably translucent. In use, the breast shield is placed over the breast and held in position by a brassiere. With reference to FIGS. 2 and 3, the detailed construction of base 10 and cover 20 can be seen.

Base 10, substantially circular, has a concave breast confronting surface 30 and a convex surface 32. A central circular aperture 34 provides clearance for the nipple to pass through. The edge of base 10 surrounding aperture 34 is rounded so as not to present any sharp edges which could injure the nipple when the breast shield is removed or shifted transversely.

Projecting outwardly from convex surface 32 (i.e., away from the breast) is peripheral lip 36 having a portion 40 remote from surface 32 whose thickness is reduced from the outside. The transition between the breast confronting surface 30 and the peripheral lip 36 is accomplished smoothly by having peripheral portion 44 curved in the opposite direction to that in which surface 30 is curved.

Cover 20, which overlies base 10, has a concave chamber defining surface 50 and an outer convex surface 54. Concave chamber defining surface 50 is surrounded by peripheral lip 58 which extends away from surface 50 (i.e., toward base 10), while providing an overall external diameter the same as that of base 10.

Peripheral lip 58 has a thickness that corresponds to the reduction in thickness of peripheral lip 36. Moreover, the outer diameter of portion 40 of peripheral lip 36 corresponds closely to the inner diameter of peripheral lip 58, so as to allow a snug mating wherein peripheral lip 58 fits around portion 40 of peripheral lip 36 and is held by friction. Complementary threads or ridges could be used, rather than relying on a friction fit. When base 10 and cover 20 are assembled in this fashion, an interior chamber, designated by reference numeral 60 in FIG. 4, is formed. It is into this chamber that excess milk seeping from the breast is collected. Cover 20 does not contact the nipple that passes through aperture 34. Thus, the nipple is shielded from possibly irritating contact with the wearer's clothing.

Cover 20 has an orifice 64, typically ⅛ inch in diameter. Surrounding orifice 64 and extending from concave chamber defining surface 50 inwardly to the interior of chamber 60 is tube 70. Tube 70, which typically has the same inside diameter as the diameter of orifice 64 may be aligned parallel to cylindrical axis of symmetry 68.

Figure 5A:
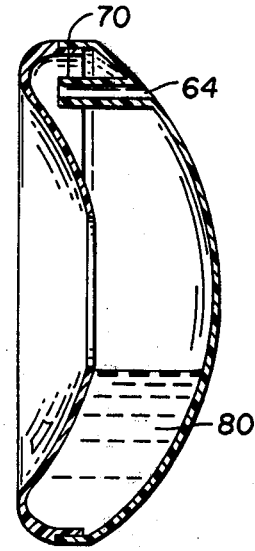
FIG. 5a is a sectional view of the milk-filled breast shield in its vertical position.

By reference to FIGS. 5a through 5d, the leakage inhibiting function of tube 70 will be understood. FIGS. 5a through 5d are sectional views of chamber 60, partially filled with milk. In FIG. 5a the breast shield is vertical with orifice 64 near the top. This is the position that the breast shield would assume under normal conditions when being worn by a nursing woman. This position presents no danger of leakage, and tube 70 is not required to prevent the flow of milk out of the chamber.

Figure 5B:
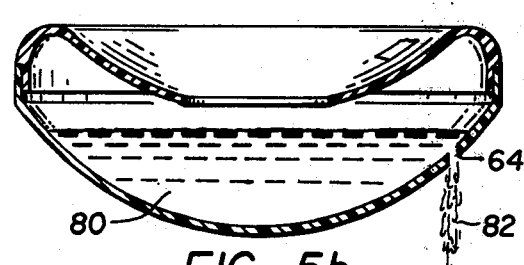
FIG. 5b is a sectional view of a milk-filled breast shield not having the tube of this invention when the breast shield is horizontal.

FIG. 5b illustrates a breast shield having an orifice 64 without a surrounding tube, when the breast shield is in a horizontal position. This orientation occurs when a woman wearing the breast shield bends over or lies down on her stomach. Milk 80 runs out of orifice 64 as a stream or series of drops 82.

Figure 5C:
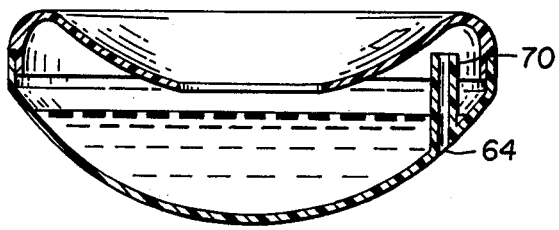
FIG. 5c is a sectional view of the milk-filled breast shield in a horizontal position.

FIG. 5c shows a breast shield according to this invention when it is in the same horizontal position as that shown in FIG. 5b. Tube 70 surrounding orifice 64 extends beyond the level of accumulated milk, thereby preventing milk from flowing out of orifice 64.

Figure 5D:
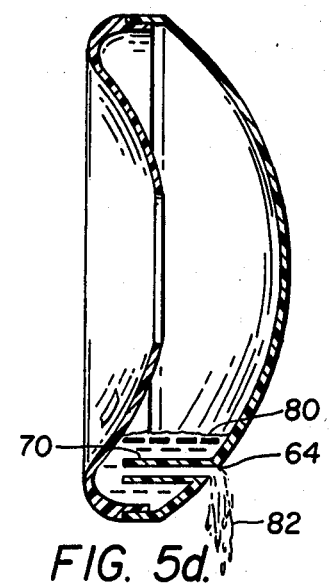
FIG. 5d is a sectional view of the milk-filled breast shield in an inverted position for emptying.

FIG. 5d illustrates the breast shield of this invention with the orifice and tube at the lowest position. Thus, should the user wish to recover the milk accumulated in the chamber, all she need do is orient the breast shield so that tube 70 is entirely below the surface of the accumulated milk. In this orientation, milk 80 flows through tube 70 and out of orifice 64 in a stream or series of drops 82.

What is claimed is:

1. In a generally circular breast shield for nursing women, said breast shield including a substantially round base having a first concave breast-confronting surface, a second convex chamber-defining surface, and a first peripheral lip surrounding said convex chamber-defining surface, said base having a centrally located nipple-receiving aperture communicating between said first breast-confronting surface and said second chamber-defining surface, said base having a cylindrical symmetry axis that is generally horizontal when said breast shield is in use on a non-reclining woman, said breast shield also including a substantially round cover having a first concave chamber defining surface, a second peripheral lip surrounding said first concave chamber-defining surface, and a second outer convex surface, said cover having a non-centrally located orifice communicating between said first chamber defining surface and said outer surface, said base and said cover being connectable by engagement of said peripheral lips to provide an inner milk receiving chamber, said breast shield in use on a non-reclining woman being disposed generally vertically with said orifice at an elevation above said aperture, the improvement comprising:

a straight tube sealingly mounted to said cover and surrounding said orifice, said tube extending away from said first concave chamber defining surface of said cover into said chamber in a direction generally parallel to said cylindrical symmetry axis said tube having sufficient length to prevent milk accumulated within said chamber from flowing through said orifice when said breast shield is tilted horizontally so that said milk surrounds said orifice, said orifice being positioned sufficiently close to the periphery of said chamber to allow a major portion of said milk to flow through said tube and said orifice when said breast shield is vertically disposed with said orifice at an elevation below said aperture.

2. The invention of claim 1 wherein said tube and said cover are of one-piece construction.

* * * * *